(12) United States Patent
Lucas

(10) Patent No.: US 10,525,175 B2
(45) Date of Patent: Jan. 7, 2020

(54) SYSTEM FOR CLEARING SURGICAL CHEST DRAINAGE TUBE BLOCKAGES

(71) Applicant: Epic Medical Concepts & Innovations, Inc., Mission, KS (US)

(72) Inventor: James R. Lucas, Mission, KS (US)

( * ) Notice: Subject to any disclaimer, the term of this patent is extended or adjusted under 35 U.S.C. 154(b) by 100 days.

(21) Appl. No.: 15/249,337

(22) Filed: Aug. 26, 2016

(65) Prior Publication Data

US 2017/0128640 A1    May 11, 2017

Related U.S. Application Data

(60) Provisional application No. 62/211,153, filed on Aug. 28, 2015.

(51) Int. Cl.
| | |
|---|---|
| *A61M 1/00* | (2006.01) |
| *A61M 25/00* | (2006.01) |
| *A61M 27/00* | (2006.01) |
| *A61M 39/00* | (2006.01) |
| *A61M 39/10* | (2006.01) |
| *A61M 39/24* | (2006.01) |

(52) U.S. Cl.
CPC .......... *A61M 1/0041* (2013.01); *A61M 1/008* (2013.01); *A61M 1/0043* (2013.01); *A61M 39/00* (2013.01); *A61M 39/10* (2013.01); *A61M 2039/2406* (2013.01); *A61M 2210/101* (2013.01)

(58) Field of Classification Search
CPC .... A61M 1/0041; A61M 1/008; A61M 27/00; A61M 25/0068; A61M 2025/0019; A61M 16/0463; A61M 2209/10; A61B 90/70; A61B 2090/701; A61B 1/122; A61B 1/121; A61B 1/267
See application file for complete search history.

(56) References Cited

U.S. PATENT DOCUMENTS

| | | | | |
|---|---|---|---|---|
| 4,573,965 | A | * | 3/1986 | Russo ................... A61M 27/00 604/128 |
| 4,696,296 | A | * | 9/1987 | Palmer ............... A61M 16/0463 128/207.16 |
| 4,850,350 | A | * | 7/1989 | Jackson .............. A61M 1/0043 128/207.16 |
| 4,960,412 | A | * | 10/1990 | Fink ................... A61M 39/0606 604/167.04 |
| 5,073,164 | A | * | 12/1991 | Hollister ............. A61M 1/0043 604/43 |
| 5,300,043 | A | * | 4/1994 | Devlin ................ A61M 1/0043 604/250 |
| 5,370,610 | A | * | 12/1994 | Reynolds ............ A61M 25/003 604/43 |
| 5,531,712 | A | * | 7/1996 | Malcolm ............. A61M 1/0031 137/505.39 |
| 5,653,231 | A | * | 8/1997 | Bell ..................... A61M 1/008 128/207.15 |

(Continued)

*Primary Examiner* — Adam Marcetich
(74) *Attorney, Agent, or Firm* — The Law Firm of Brett M. Maland

(57) ABSTRACT

This device is used to clear clots and blockages from chest drainage tubes. This invention relates to patient safety after open-heart surgical procedures, wherein postoperative drainage from the surgical site is a critical component of care. Blocked drainage tubes can cause dangerous retained blood complications, most notably, cardiac tamponade, which essentially smothers the heart.

5 Claims, 4 Drawing Sheets

(56) References Cited

U.S. PATENT DOCUMENTS

| | | | |
|---|---|---|---|
| 5,919,174 A * | 7/1999 | Hanson | A61M 16/0463 251/320 |
| 6,923,184 B1 * | 8/2005 | Russo | A61M 16/0463 128/200.26 |
| 7,779,842 B1 * | 8/2010 | Russo | A61M 16/0463 128/205.19 |
| 7,854,728 B2 | 12/2010 | Boyle, Jr. | |
| 7,951,243 B2 | 5/2011 | Boyle, Jr. et al. | |
| 8,048,233 B2 | 11/2011 | Boyle, Jr. et al. | |
| 8,246,752 B2 | 8/2012 | Boyle, Jr. | |
| 8,388,759 B2 | 3/2013 | Boyle, Jr. et al. | |
| 2001/0029953 A1 * | 10/2001 | Mattar Neto | A61M 16/0463 128/207.16 |
| 2004/0082923 A1 * | 4/2004 | Field | A61M 16/0463 604/267 |
| 2004/0230169 A1 * | 11/2004 | Felix | A61M 1/0047 604/317 |
| 2006/0130847 A1 * | 6/2006 | Morejon | A61M 16/0463 128/207.15 |
| 2008/0185006 A1 * | 8/2008 | Harand | A61M 16/0463 128/207.16 |
| 2009/0287151 A1 * | 11/2009 | Resca | A61M 16/0463 604/119 |
| 2010/0186748 A1 * | 7/2010 | Morejon | A61M 16/0463 128/207.14 |
| 2015/0231287 A1 * | 8/2015 | Lin | A61L 2/10 607/80 |
| 2016/0001036 A1 * | 1/2016 | Nickerson | A61M 25/00 604/540 |
| 2016/0256646 A1 * | 9/2016 | Vazales | A61B 1/267 |

\* cited by examiner

SYSTEM FOR CLEARING SURGICAL CHEST DRAINAGE TUBE BLOCKAGES

CROSS REFERENCE TO RELATED APPLICATION

This document claims priority to U.S. Provisional Patent Application No. 62/211,153 titled "System for Clearing a Chest Drainage Tube" filed on Aug. 28, 2015.

FIELD

This document relates to the field of medical devices and more specifically, cleaning devices for chest drainage tube blockages.

BACKGROUND

Blocked chest drainage tubes can cause dangerous retained blood complications, most notably, cardiac tamponade, which essentially smothers the heart. A major drawback to passive drainage systems is that clots quickly develop within the tubing, which prevent proper drainage. Critical care nurses are trained to manually manipulate and "strip" the tube by hand ever 15-30 minutes, but this method is time-consuming and largely ineffective, because several inches of the drainage tube are actually under the patient's skin. It also depends on the nurse remembering to do the required stripping and tube maintenance.

Previous work in this field (U.S. Pat. Nos. 7,854,728, 7,951,243, 8,246,752, 8,048,233 and 8,388,759) allude to the same general problem, but use a different methodology for active clearance. In the referenced invention, a wire catheter with angled, looped tip is advanced through the chest tube and use to "scrape" the inside of the chest tube. However, in practice this has been problematic for a variety of reasons. Particularly, the wire loop tends to allow clots to form on itself, and the clotted loop can itself block the drainage tube, as well as push clots into the chest cavity when advancing the catheter.

SUMMARY

Disclosed herein is a chest drainage tube catheter apparatus that effectively removes clots and other blockages from chest drainage tubes. The disclosed apparatus employs a vacuum delivered via a catheter allowing the catheter to not only loosen debris by contact with the catheter, but the vacuum allows this catheter to suck away dots and debris and remove the debris from the chest drainage tubes.

In the preferred embodiment, the catheter apparatus incorporates several innovative elements in addition to the vacuum connection including a vacuum throttling valve, a backflow preventer, a collapsible sheath, a normally closed switch, and a y-connector with a secondary vacuum connection.

The catheter apparatus is easy to use and can be operated by a single operator. An operator can use a first hand to hold the catheter at a desired level with at least one or more fingers on the switch so that the switch can be activated or opened by pressing the switch with a finger or fingers. An operator may use a second hand for threading the catheter into a chest drainage tube. While threading the catheter into the chest drainage tube and while later pulling the catheter out of the chest drainage tube with the same second hand, the operator may press the switch using the first hand to activate the vacuum whenever the operator detects debris. More preferably, the operator may use the first hand to press into the second hand, thereby collapsing the apparatus, using the second hand to position the catheter into the drainage tube.

DETAILED DESCRIPTION OF DRAWINGS

Figure 1A:
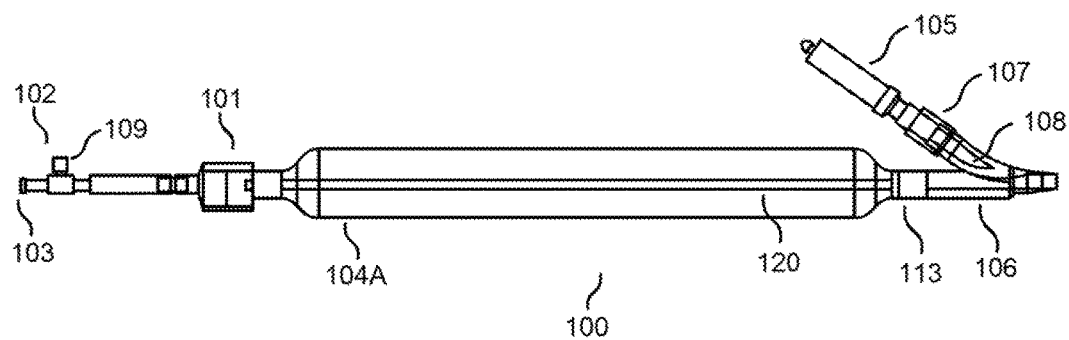
FIG. 1A shows the catheter apparatus wherein the catheter is inside the sheath.
Figure 1B:
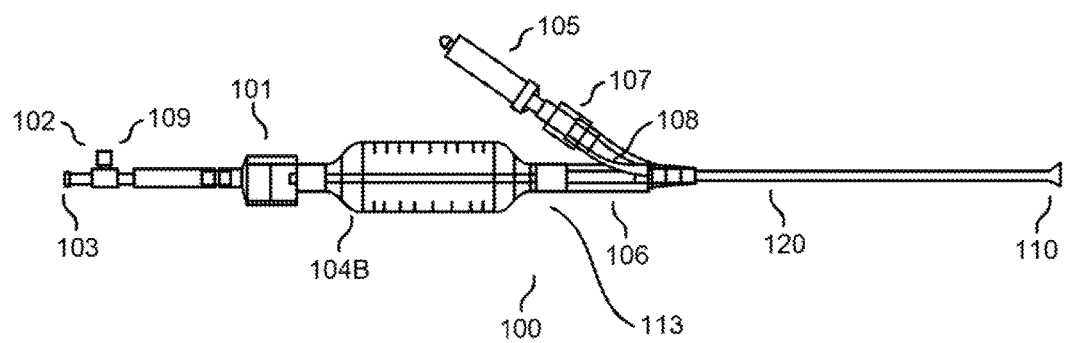
FIG. 1B shows the catheter apparatus wherein the catheter is engaged and is outside the sheath so that the catheter may be inserted into a drainage tube.

Referring to FIG. 1A and FIG. 1B, the catheter apparatus 100 delivers vacuum or suction through a catheter configured to clear drainage tubes, such as drainage tubes used to drain fluids from a patient after surgery. In the preferred embodiment, the catheter apparatus 100 is comprised of a vacuum inlet 103, a vacuum throttling valve, an on/off switch 101, a sheath 104, and a clearing mechanism, all supporting a catheter 120. The cleaning mechanism is comprised of a y-connector 106 that is connected to a vacuum system via a secondary vacuum inlet 107 to deliver a vacuum to a secondary vacuum tip 108 that is capable of vacuuming fluids from the outside of the catheter 120. In the most preferred embodiment, a backflow preventer 105 prevents contamination from the vacuum system from being applied to the catheter 120. The sheath 104 covers the catheter and is sealed at 113 from the y-connector 106.

Figure 2:
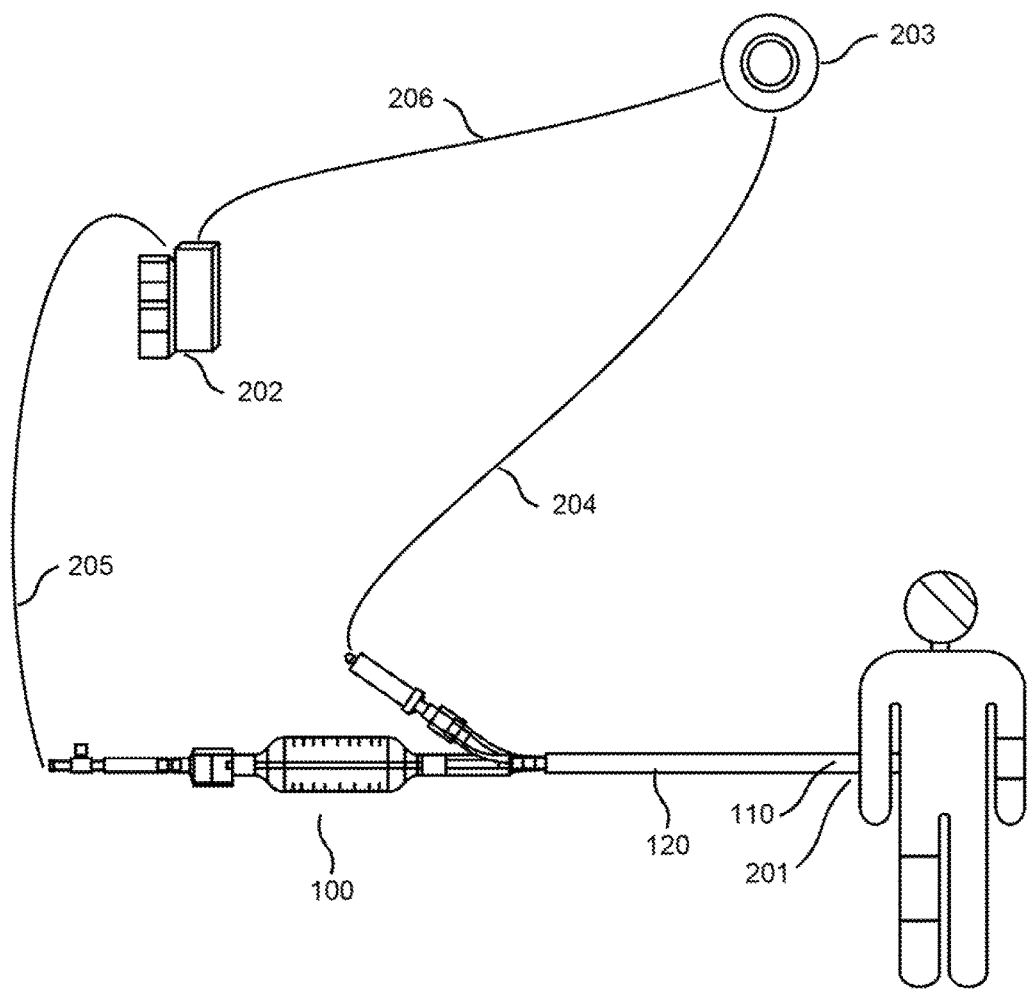
FIG. 2 shows the catheter apparatus wherein the apparatus is engaged with existing hospital infrastructure and is engaged in a patient's chest drainage tube.

The catheter apparatus 100 can be connected to a standard vacuum system 203 at a hospital, as diagramed in FIG. 2. The catheter apparatus 100 is connected to a collection chamber 202 via a first vacuum line 205, and the collection chamber 202 can in turn be connected to the vacuum system 203 via a second vacuum line 206. The cleaning mechanism on the catheter apparatus can be connected directly to the vacuum system 203 via a secondary vacuum line 204, as it will typically have only minimal amounts of fluid or debris, which would could be handled by the hospital vacuum system 203 and wall collection chambers. However, the cleaning mechanism could also be connected to the collection chamber 202.

To use the apparatus, an operator, typically a nurse or other health professional, holds the proximal end of the apparatus, near the switch 101, with a first hand, keeping one finger on the switch 101. The operator's second hand can then be used to support the distal end of the catheter 120, near the y-connector. By pushing the proximal end into the distal end, the sheath 104A collapses into sheath 104B, which in turn pushes the catheter 120 into a chest drainage tube 201. The operator may also thread more of the catheter 120 through the switch using the first hand. If debris or fluid is encountered, the operator may use a finger on the first hand, typically a thumb, to engage the switch 101 so that a vacuum is applied to the catheter 120, which is delivered to the chest drainage tube 201, vacuuming out any debris. In the preferred embodiment, the catheter 120 has a flared tip 110 for effective cleaning.

As the operator pushes the catheter 120 into the chest drainage tube 201, the operator may intermittently engage the switch 101 to apply the vacuum to the catheter. The operator can also push the catheter 120 into the portion of a chest drainage tube 201 that is beneath the surface of a patient's skin.

In the preferred embodiment, the vacuum level can be throttled or lowered with a vacuum throttling device. The preferred throttling device is comprised of a vacuum throttling valve 102 having a threaded valve knob 109, the valve knob capable of being turned so that it restricts the air flow flowing through the vacuum throttling valve 102 via a relief opening inside the throttling valve 102. As the threaded valve knob 109 is tightened, more of the relief opening is closed off and vice versa. Referring back to FIG. 1A and FIG. 1B, to set up the apparatus 100, an operator should adjust the vacuum throttling valve 102 by turning the threaded valve knob 109 so that a sufficient portion of the vacuum line is restricted, which will cause the vacuum to lose energy, making the vacuum weaker. A weaker vacuum may be desired if the vacuum level from the hospital vacuum system 203 is such that it risks injuring the patient.

Figure 3A:
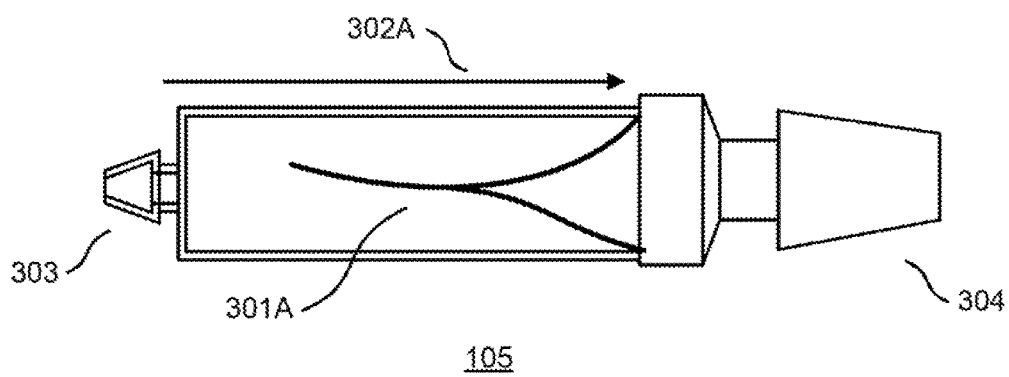
FIG. 3A shows the backflow preventer wherein the backflow preventer is preventing the flow of air.
Figure 3B:
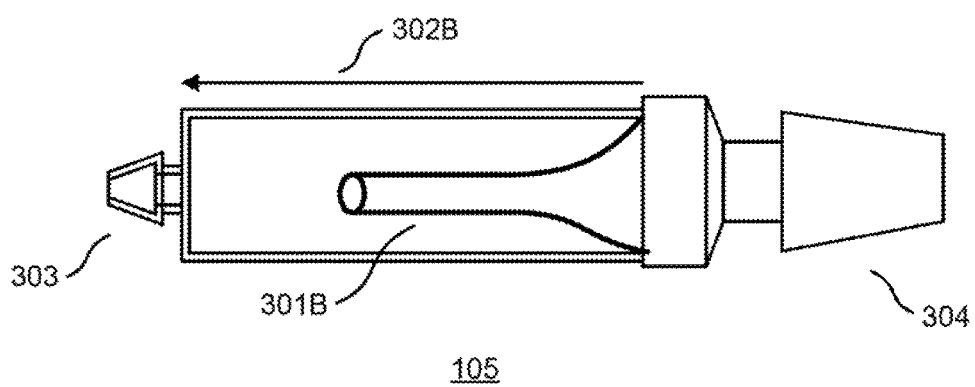
FIG. 3B shows the backflow preventer wherein the backflow preventer is allowing the flow of air.

The backflow preventer 105 is shown in more detail in FIG. 3A and FIG. 3B. The backflow preventer 105 is a cylindrical plastic chamber and has a latex valve 301B that allows air to flow in one direction 302B, but the latex valve 301A closes when air flow attempts to flow in the opposite direction 302A. The latex valve may be comprised of a latex tube about that extends about three quarters of the cylindrical plastic chamber and will naturally collapse when air starts to move in the direction 302A. The backflow preventer can be coupled to a hospital vacuum system at a first connector 303, and can be coupled to a y-connector at a second connector 304.

Figure 4A:
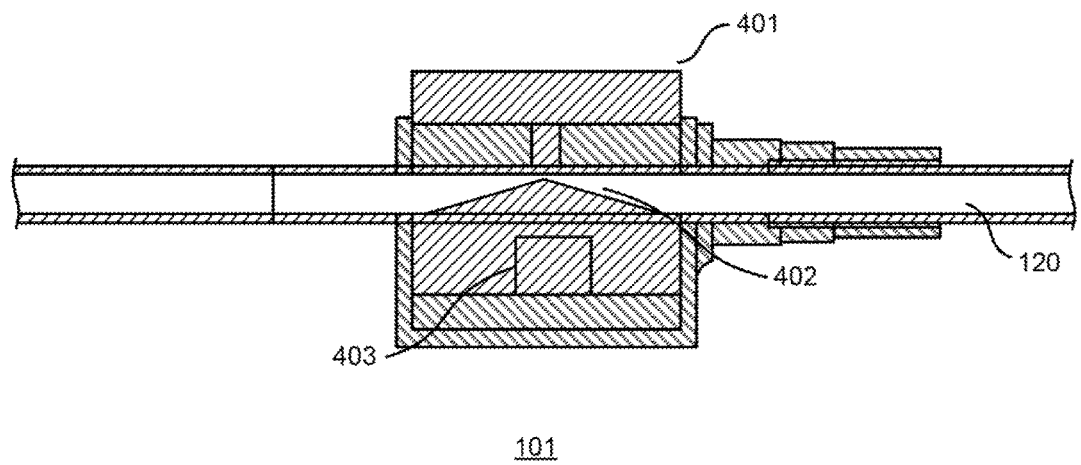
FIG. 4A shows the switch in the closed position.
Figure 4B:
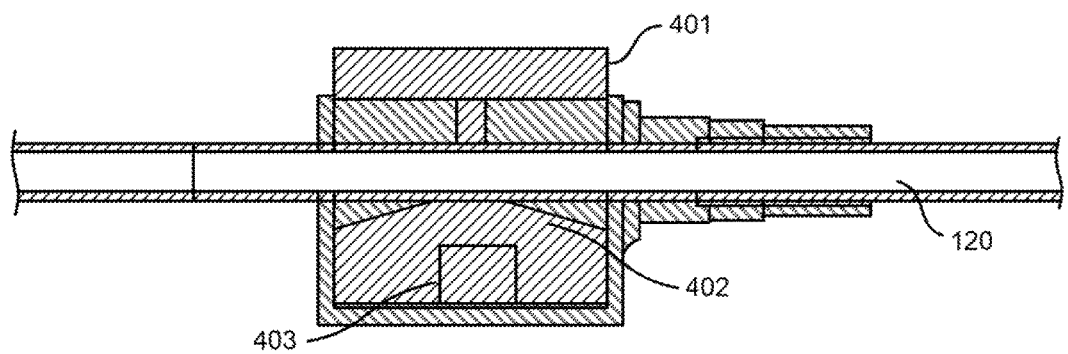
FIG. 4B shows the switch in the open position.

The switch 101 is shown in more detail in FIG. 4A and FIG. 4B. The switch 101 consists of push button 401, crimping component 402 and a spring 403. In 4A, the switch 101 is in the unengaged, and closed position because the air flow through the catheter 120 has been shut off by a crimping component 402 that is pressed into the catheter 120 by a spring 403. When the push button 401 is pressed by an operator, the push button acts upon the crimping component 402 to overcome the resistance of the spring 403. When the push button is activated or engaged, then the catheter 120 is open, and the vacuum is delivered through the catheter 120 and into the catheter 120.

In the preferred embodiment, the apparatus 100 is comprised of biocompatible plastics and K-resins, silicon, UV cured adhesives, and is sterilized with ethylene oxide prior to use. The collapsible sheath is composed of a collapsible, thin plastic, the plastic being manufactured from EtO-transparent materials to facilitate sterilization.

I claim:

1. A chest tube catheter apparatus comprising
a catheter sized to fit inside a chest drainage tube, the catheter having a proximal end and a distal end,
   the proximal end having
      a primary vacuum inlet, and
      a switch
   the distal end having a flared tip, and
a collapsible sheath having a proximal end and a distal end and enclosing at least a portion of the catheter,
wherein a y-connector is coupled to the distal end of the collapsible sheath, the y-connector having a backflow preventer coupled to the secondary vacuum inlet, the backflow preventer comprising a collapsible latex valve configured to prevent any fluid from entering the catheter from the backflow preventer.

2. The apparatus of claim 1, further comprising a vacuum throttling valve configured to regulate the vacuum level in the catheter, and wherein the switch has a push button, the push button capable of opening the proximal end of the catheter when activated, and wherein the vacuum throttling valve and the switch are located on the proximal end of the catheter.

3. The apparatus of claim 1, wherein the sheath is configured to collapse and wherein the y-connector is under vacuum supplied by a secondary vacuum inlet, the sheath being sealed from the vacuum created by secondary vacuum inlet.

4. A catheter apparatus comprising
a vacuum catheter configured for clearing chest drainage tubes, the vacuum catheter having a proximal end capable of connecting to a vacuum supply and a distal end sized to fit inside chest drainage tubes and having a flared tip, an extendible sheath and a y-connector enclosing at least a portion of the vacuum catheter,
a vacuum throttling valve located on the proximal end of the catheter configured to regulate the vacuum level in the vacuum catheter, the vacuum throttling valve being coupled to the vacuum catheter, and
a switch located on the proximal end of the catheter configured to open and close the connection to the vacuum supply
wherein the y-connector has a first connection, a second connection, and a third connection, wherein the first and second connections enclosing at least a portion of the vacuum catheter, and wherein the third connection has a secondary vacuum inlet and a secondary vacuum tip configured for cleaning the vacuum catheter, and wherein the third connection is further coupled to a backflow preventer configured to prevent fluid from traveling from the backflow preventer to the catheter.

5. The catheter apparatus of claim 4, wherein the backflow preventer has a collapsible latex valve.

\* \* \* \* \*